United States Patent
Dey et al.

[11] Patent Number: 6,004,509
[45] Date of Patent: Dec. 21, 1999

[54] PROCESS FOR MAINTAINING THE STERILITY OF A MEDICAL INSTRUMENT

[75] Inventors: Uwe Dey; Bernd Müller; Peter Hartwig, all of Berlin; Torsten Thiel, Fürstenwalde, all of Germany

[73] Assignees: DMV-Medizintecknik GmbH, Hennigsdorf; Jakoubek Medizintechnik GmbH, Liptingen, both of Germany

[21] Appl. No.: 08/616,553

[22] Filed: Mar. 15, 1996

[30] Foreign Application Priority Data

Mar. 15, 1995 [DE] Germany ............ 195 10 707

[51] Int. Cl.⁶ .................................................. A61L 2/20
[52] U.S. Cl. .................. 422/28; 134/22.12; 422/33; 600/560; 604/23; 604/26
[58] Field of Search ............... 422/3, 28, 33; 134/22.12; 604/23–26; 600/158, 560

[56] References Cited

U.S. PATENT DOCUMENTS

| | | | |
|---|---|---|---|
| 4,216,767 | 8/1980 | Aoshiro | 422/33 |
| 4,598,698 | 7/1986 | Siegmund | 604/26 |
| 4,715,372 | 12/1987 | Philippbar et al. | 128/303.1 |
| 5,037,386 | 8/1991 | Marcus et al. | 604/43 |
| 5,103,804 | 4/1992 | Abele et al. | 604/114 |
| 5,137,509 | 8/1992 | Freitas | 604/26 |
| 5,246,419 | 9/1993 | Absten | 604/26 |
| 5,290,308 | 3/1994 | Knight et al. | 606/205 |
| 5,354,302 | 10/1994 | Ko | 606/104 |
| 5,514,087 | 5/1996 | Jones | 604/26 |
| 5,800,381 | 9/1998 | Ognier | 604/26 |
| 5,849,005 | 12/1998 | Garrison et al. | 604/26 |

FOREIGN PATENT DOCUMENTS

| | | |
|---|---|---|
| 0165472 | 12/1985 | European Pat. Off. . |
| 0316593 | 5/1989 | European Pat. Off. . |
| 0407820 | 1/1991 | European Pat. Off. . |
| 2318860 | 10/1974 | Germany . |
| 2547185 | 4/1977 | Germany . |
| 3611018 | 6/1987 | Germany . |
| 3738692 | 6/1989 | Germany . |
| 9105399 U | 10/1991 | Germany . |
| 9109909 U | 11/1991 | Germany . |
| 3880133 | 9/1993 | Germany . |
| 9314104 U | 5/1994 | Germany . |

*Primary Examiner*—Peter A. Hruskoci
*Attorney, Agent, or Firm*—Venable; George H. Spencer; Catherine M. Voorhees

[57] ABSTRACT

Process for maintaining the cleanliness of the inner cavity of a medical operating instrument (I), particularly a surgical instrument used in minimally invasive medicine, having an outer casing (M) and operating or actuating elements (SS, SH) arranged therein, said instrument being used to enter the body of a living person or animal, wherein during its use the instrument is acted upon essentially from its proximal end through a fluid connection (A) with a medically clean fluid (G) in such a way that essentially all the crevices and cavities in the inner space, in fluid contact with the inside of the body, between the operating or actuating elements (SS, SH) or between the latter and the casing (M) are filled with the fluid.

5 Claims, 5 Drawing Sheets

PROCESS FOR MAINTAINING THE STERILITY OF A MEDICAL INSTRUMENT

BACKGROUND OF THE INVENTION

The invention relates to a process for maintaining the sterility of a medical instrument, particularly in minimally invasive medical procedures, as well as an apparatus for carrying out the process.

In recent years, medical procedures, particularly operating techniques which make do with very small incisions in the body of the person or animal being treated, have acquired considerable importance and a completely new branch of medicine has arisen, so-called minimally invasive medicine.

The instruments used in this, such as endoscopes, arthroscopes, special endoscopic gripping and cutting devices, are designed for insertion in the body and for handling through a small incision and comprise parts which are inserted in particular in small diameter sleeves and in some cases are movable in the sleeves.

During the manipulation of the instruments in the patient's body it frequently occurs that body fluid enters the interior of the instrument, because of the capillary forces in the narrow gaps between the individual parts, leading to contamination. This internal contamination is very difficult or even impossible to remove once the procedure has ended and the sterility required can only be achieved under certain conditions. The practical service life of these expensive high precision instruments is therefore frequently far less than their actual technical service life.

In minimally invasive procedures in humans or animals, e.g. in the abdominal region (in laparoscopy), in the uterus (in hysteroscopy) or in the joints (in arthroscopy) it is necessary to widen the existing cavity by means of a gas, for which carbon dioxide is preferably used. The space thus formed creates a wide enough area of operation or observation allowing the operator to carry out the necessary medical interventions through the above-mentioned small access openings into the body cavity or into the organ or blood vessel.

This increase in pressure, which is unavoidable in order to achieve the necessary operating conditions in the majority of minimally invasive procedures, means that the pressure prevailing in the body cavity forces contaminated insufflation gas and/or body fluid into the instruments or endoscopic equipment used in the operation.

This further exacerbates the above mentioned problem of the internal contamination of the instruments.

SUMMARY OF THE INVENTION

The aim of the invention is therefore to provide a method of largely maintaining the sterility of the interior of medical instruments as are used particularly in minimally invasive surgery and to provide an apparatus for carrying out the process.

This is achieved by means of a process and an apparatus characterised in that during use of the instrument a medically clean fluid is introduced substantially to a proximal end of the instrument through a fluid connection in such a way that essentially all crevices and cavities in an inner space of the instrument, in fluid contact with the inside of the body, between the operating or actuating elements and the casing are filled with the fluid.

The invention includes the finding that the penetration of body fluid and/or gases containing bodily substances during medical intervention into the instrument or apparatus used can be prevented if the gaps, channels or cavities present in the surgical instrument are filled with an agent or acted upon by pressure to counteract the penetration of the contaminated gas or body fluid from the area of intervention into the instrument.

This gives rise to the possibility in particular of introducing a medically clean gas into the gaps and cavities of the instrument under a pressure which is directed counter to the capillary force acting in the instrument or the pressure prevailing in the insufflated body cavity and which is at least equal in magnitude. This procedure is hereinafter referred to as instrument insufflation for short.

In connection with this it is particularly easy and convenient if the apparatus which is used in any case in the operation for the insufflation of gas (to expend the body cavity or organ or blood vessel) is used at the same time to prepare the gas which is to act upon the instruments and equipment used in the operation.

The chief advantage of this is that sterilising gas is always available under the correct pressure for instrument insufflation, irrespective of the operational condition of the equipment, and there is no need for any additional equipment, requiring separate adjustment, to produce pressure for insufflation of the surgical instruments or endoscopic equipment.

According to an advantageous embodiment of the invention the apparatus for carrying out the process according to the invention is therefore a gas insufflator having a pressurised store for the insufflation gas an apparatus for maintaining a constant pressure in the gas which can be taken from the pressurised store through a gas pipe, a first tube connection to which an insufflation trocar or a veress needle can be connected by means of a gas hose, and a second tube connection which can be connected via a separate gas hose to the proximal end of a surgical or diagnostic instrument or apparatus.

It may also be useful to provide additional branches on the second tube connector or on the second gas hose in order to allow pure gas to act on a number of instruments at the same time and thereby keep them internally clean. This makes handling easier in operations in which a number of different instruments have to be used.

From the point of view of design and technology it is particularly useful if the tube connectors for the expansion insufflation and the connection or connections for the instrument insufflation are connected in parallel inside the apparatus. This is a simple way of ensuring there is always a pressure available for the instrument insufflation which is in a specific ratio to the pressure generated by the gas insufflation in order to prepare the operating area inside the body cavity, organ or blood vessel.

According to another embodiment of the invention, for an existing insufflation device an additional device is provided which can be connected to the tube connection of the insufflation arrangement. The additional device comprises an inflow channel and at least two outflow channels, one of which is connected to the actual insufflation trocar whilst the other or others is or are connected with the surgical or diagnostic instrument or instruments.

This ensures that there is always a substantially equal pressure available for the two different insufflation tasks, i.e. the expansion insufflation and the cleaning or instrument insufflation, irrespective of the operational state of the pressure control means of the insufflation device.

If the instrument insufflation requires a gas pressure which is different from that of the expansion insufflation, the corresponding outflow channel has, according to another advantageous embodiment, an additional regulator which can be actuated for example by a pressure sensor located in the body cavity or organ acted upon by the gas insufflation.

The control or regulation of the gas pressure for the expansion insufflation and the instrument insufflation is preferably carried out by taking into account the non-linear dependency of the flow resistance of the insufflation means as a function of the volume flow of the gas (gas flow). Control or adjustment can thus be carried out essentially without any pure measuring phases, i.e. interruption of the introduction of gas into the body and the instrument, which is of great importance in keeping the instruments reliably clean.

The admissible internal pressure in the body—from which the gas pressure for the instrument insufflation is also to be obtained as explained above—is determined without any separate internal measurement of the body by suitable correction of the insufflation pressure which is measured essentially continuously (using the gas supply line in the apparatus) with a correction magnitude which reflects the fall in pressure caused by the special insufflation system (including trocar or veress needle and taking account of the instrument inputs) and the flow-dependent dynamic pressure component. The correction magnitude is taken as a characteristic value of a predetermined characteristic curve.

Technical measurements have shown that the characteristic curve is essentially parabolic and conforms to the equation $$\Delta p = K \times Q^z$$

$\Delta p$ designating the pressure drop in the insufflation system, Q denoting the gas flow measured and K or z being constants which reflect the flow properties arising from the geometry of the gas supply line or the attached insufflation instrument, e.g. a trocar or a veress needle.

For various trocars and/or connecting tubes, for example, there is a family of characteristics which can be determined in advance and stored in the equipment, at least for the components which are used frequently. The choice of characteristic curve belonging to the particular insufflation system used can be made by manual inputting in the equipment or—preferably before the start or during the first phase of the introduction of the gas—by a calibrating measurement.

The calculation is made in a microcomputer having a characteristic memory from which the data representing the family of characteristics are retrieved for a computer-aided comparison of the measurements obtained during gas flow variation.

The two constants K and z can be determined on the one hand, when changing the insufflation instrument, by insufflating twice against the ambient pressure from two pairs of measurements or, on the other hand, for a variety of gas supply lines and insufflation instruments by means of a series of calibrating measurements.

In this way it is possible to determine the drop in pressure as a function of the gas flow beforehand experimentally, for all kinds of practically usable modifications of the insufflation system, and to store these values in readiness.

The apparatus for performing the process described above with advantageous control or regulation of pressure comprises in particular a device for (preferably continuously) measuring the gas throughput per unit of time and a memory device for recording the characteristic value or values, by means of which the correction magnitude for indirectly determining the internal body pressure can be calculated from the gas flow measured.

In one particularly economical embodiment the first pressure sensor for determining the insufflation pressure in order to produce the gas flow measuring device has a second pressure sensor associated with it, and between the measuring points of the two pressure sensors in the gas supply line is a flow resistance element. This generates a defined fall in pressure or differential pressure from which the volume throughput per unit of time (gas flow value) is then determined in a manner known per se.

The pressure values obtained by means of the first and second pressure sensors are used to form a differential pressure and, in order to calculate the gas flow value, they are supplied to the processing unit which is provided with hardware or software in order to perform the calculation. The gas flow values form the basis for calculating the internal pressure in the organ, body cavity or blood vessel acted upon by the gas, especially carbon dioxide, as explained above, together with the insufflation pressure in the apparatus which is measured at the same time.

According to a favourable embodiment of the invention which allows versatile use of the apparatus in a wide range of very small gas throughputs (up to 0.1 l/min in hysteroscopy) through moderate (around 2 l/min in arthroscopy) up to very great gas throughputs (up to about 30 l/min in laparoscopy), a plurality of parallel connected flow resistance elements are provided in order to expand the range of measurements. These flow resistance elements, which may take the form of shutter valves or sintered material inserts, for example, are each arranged in a branch line of the gas supply line which can be closed off by means of controllable valves. By electrically actuating the valves using the microcontroller and the control unit of the apparatus it is readily possible to switch over the measuring range, which can be determined by the nature and number of shutters or sintered inserts in one or more branches of the tube.

Moreover, the arrangement of the pressure sensors is advantageously suitable, in conjunction with the processor unit, for checking the correct operation of the pressure sensors while the apparatus is working, by means of a plausibility control. For this purpose, the processor unit contains a hardware and/or software testing program by means of which the sensors are constantly or at least periodically checked by comparing them with one another.

A plausibility control of this kind advantageously does away with the need for a third pressure sensor as a safety pressure monitor at the outlet of the apparatus.

According to another advantageous feature of the invention the pressurised gas store of the apparatus has at least two gas bottles which can be alternately connected to the gas supply line via switching means. The switching means take the form of a magnetic valve with a non return valve provided upstream of them and are controlled by means of the processor unit as a function of the pressure conditions in the gas supply line.

The apparatus may also have an associated device for treating, particularly heating, humidifying and/or filtering, the gas used for acting on the instruments or for insufflation and this treatment device may also be controlled by means of the processing and control unit of the basic apparatus.

BRIEF DESCRIPTION OF THE DRAWINGS

Advantageous features of the invention are described hereinafter in conjunction with the description of the preferred embodiment of the invention referring to the Figures, wherein.

DETAILED DESCRIPTION OF THE INVENTION

Figure 1:
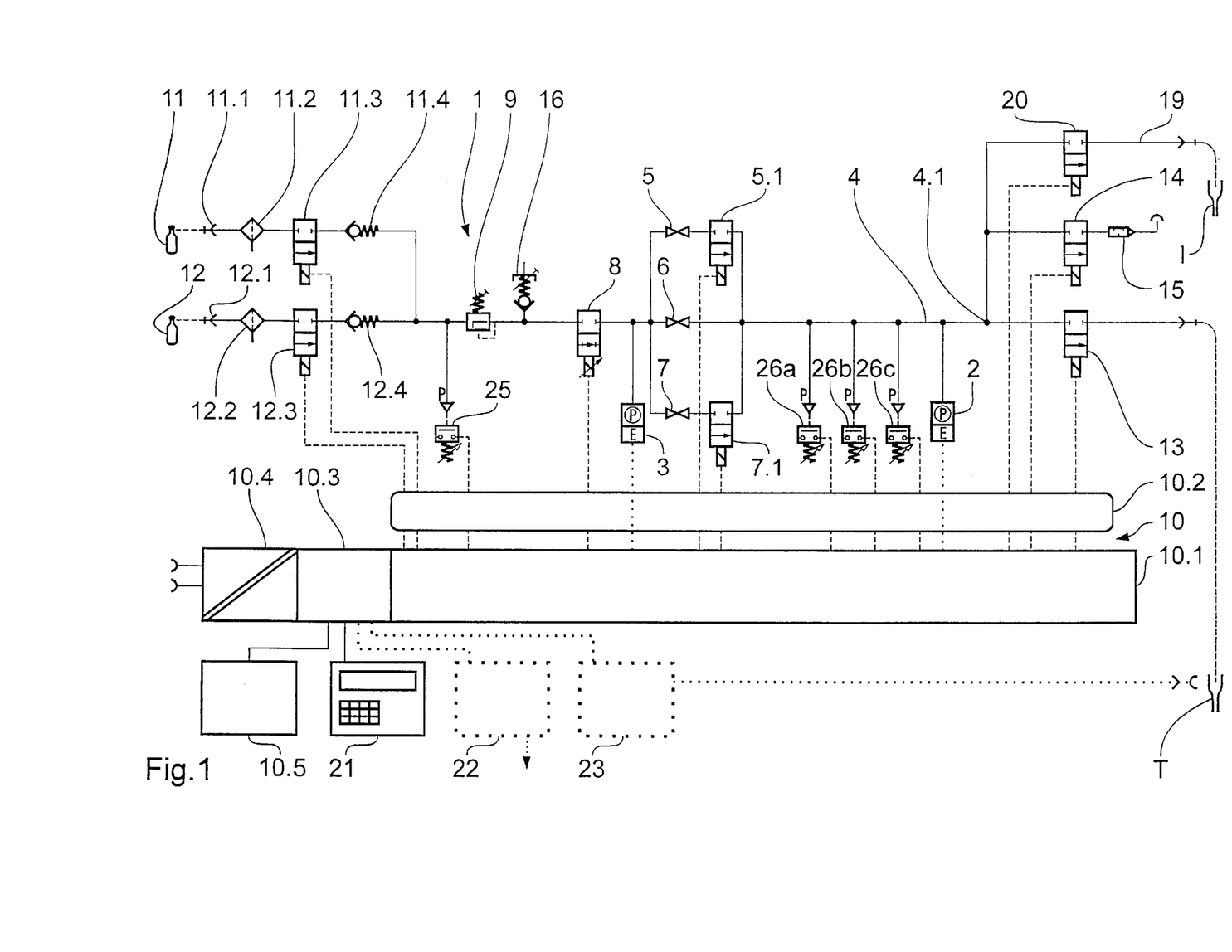
FIG. 1 is a diagrammatic view of a preferred embodiment of the invention.

The insufflation device diagrammatically shown in FIG. 1 for insufflating carbon dioxide before and during diagnostic or surgical interventions and for keeping a medical instrument clean, in which the internal pressure prevailing in the cavity or in the blood vessel is continuously determined and regulated, has a pressurised gas store with two gas bottles 11 and 12 the connections of which 11.1 and 12.1 are each connected to a gas supply line 4 via a filter 11.2 and 12.2, a solenoid 11.3 and 12.3 and a non-return valve 11.4 and 12.4.

Connected to a free end of the gas supply line 4, via a gas hose, is an insufflation trocar T for introducing the gas into the patient's body for the purpose of opening out the area, organ or blood vessel which is to be treated.

Proceeding from a branch point 4.1 close to this end of the gas supply line is a separate tube branch 19 which leads, again via a gas hose, to an instrument I which is to be acted upon by the insufflation gas in order to keep its interior clean. The tube 19 is closable for cases when the insufflation device 1 is to be used without instrument insufflation or, in the event of a defect, by means of an electrically actuated locking valve 20.

In the gas supply line 4, downstream of the gas bottles, for monitoring the pressure therein, there is a high pressure switch 25 the output of which is connected to a processing unit 10 of the equipment. In the event of a deficiency of gas in the particular gas bottle 11 or 12 connected to the gas supply line 4, there is an appropriate optical and/or acoustic signal by means of the processing unit 10 and an associated operating and display area 21. The other bottle 12 or 11 can then be connected up to the gas supply line either manually or automatically, if the warning signal having been processed by the processor unit and converted in the associated control unit 10.2 is simultaneously used as a control signal for the solenoid 11.3 or 12.3.

A high pressure reducer 9 provided downstream, having an excess pressure safety device 16, reduces the gas pressure in the gas supply line 4 to a level in the lower bar region. If the high pressure reducer 9 fails an overpressure safety device 16 downstream thereof is actuated and opens the gas supply line 4 to atmosphere.

A proportional valve 8 provided downstream of the high pressure reducer 9 and the overpressure safety device 16 is operated in cooperation (as described more precisely hereinafter) with pressure sensors 2 and 3 (arranged further downstream) as a pressure regulating device, the proportional valve 8 being actuated via the microcomputer (microcontroller) 10.3 and the control part 10.2 of the processor unit 10.

The pressure sensors 2 and 3, the outputs of which are connected to separate inputs of the processor unit 10 (more accurately: the analogue processing part 10.1) form a differential pressure gauge together with flow resistors 5, 6, 7 arranged between them and connected in parallel to one another in branches of the gas supply line.

The gas flow present in the gas supply line 4 is calculated in the processing unit from the pressure values obtained upstream and downstream of one of the flow resistors. The flow resistors 5, 6, 7 connected in parallel are each constructed as a calibrated shutter or sintered insert with greatly differing flow resistance levels and can be switched on or off by actuation of a solenoid 5.1 or 7.1 provided in the corresponding branch of the tube, by means of the operating area 21 and the microcontroller 10.3. In this way the measuring range can easily be switched over so that a gas flow ranging from a few tens of millilitres up to about 40 litres per minute can be measured.

The pressure sensor 2 mounted downstream of the flow resistors serves simultaneously to detect the insufflation pressure.

A major advantage of the apparatus 1 for gas insufflation shown is the double function of this pressure sensor which is used—together with the second pressure sensor 3 instead of a conventional differential pressure sensor—to determine the differential pressure in order to calculate the gas throughput per unit of time (gas flow) and also at the same time sends the actual valve of the insufflation pressure to the processor unit 10.

In the processor unit 10 the pressure sensor signals are prepared and the gas flow valve is calculated from the difference between the pressures determined by the first and second pressure sensors. In addition, as described above, the appropriate characteristic curve for the specific insufflation system is selected here in order to determine the internal pressure from a plurality of characteristic curves stored in a characteristic memory 10.5 for the functional correlation between the drop in pressure caused by the insufflation system (more precisely that part which extends from the measuring point of the pressure sensor 2 to the patient's body) and the gas flow.

Finally, the internal body pressure to be determined here is calculated from the insufflation pressure measured and the fall in pressure taken from the appropriate characteristic curve for the gas flow which is measured (indirectly by means of the pressure sensors 2 and 3) and this is displayed on the operating and display field 31 and fed into the control part 10.2 in order to operate the proportional valve 8. This operation is such that when the internal pressure values are significantly below the nominal internal pressure (during the initial phase of insufflation) a major gas throughput is achieved, whereas once the nominal internal pressure is reached there is merely sufficient insufflation to maintain the pressure with a substantially reduced gas throughput.

Moreover, the arrangement of the pressure sensors 2, 3 and the (hard- and software) construction of the microcontroller 10.3 is such that the operation of the pressure sensors 2 and 3 is monitored during operation of the equipment I by means of a plausibility check or mutual comparison of the pressure measurements.

In order to do this, preferably when the right internal pressure has already been substantially reached and only pressure maintaining insufflation is being carried out, an operational state of the apparatus is produced, by closure of the proportional valve 8, in which substantially no gas flows out of the device. Then the drop in pressure at the particular flow resistor 5, 6 or 7, detected from the measurements of the pressure sensors 2 and 3, must be approximately equal to zero, i.e. operational pressure sensors 2, 3 must yield the same measurement. The creation of a differential value which is carried out in the microcontroller after the valve 8 has been shut must therefore yield the value zero (within a given error range).

If this is not the case a warning signal is emitted via the operating and display field 21 and/or by means of the control stage 10.2 there is automatic closure of a solenoid 13 (patient valve) provided at the exit from the equipment in the gas supply line 4 or another solenoid 14 (outlet valve) provided immediately downstream of said solenoid 13 and connecting the gas supply line to atmosphere via a filter 15 is opened. (The filter 15 is intended to prevent foreign particles from outside from entering the insufflation system.)

Moreover, in order to check the function of the pressure sensors 2 and 3 it is also possible to carry out a slight increase or reduction in the gas flow periodically during insufflation by suitably actuating the proportional valve 8 in accordance with a test cycle prescribed by the microcontroller 10.3. The resulting weak pressure wave must be indicated at the same level in properly operating pressure sensors 2, 3, i.e. there must be the same change in pressure. A simple comparison of amplitudes in the processor unit 10 will yield the test signal.

In order to protect the patient and the apparatus 1 for the purposes of gas insufflation a number of electrical overpressure switches 26a to 26c with different response values are provided between the flow resistors 5, 6, 7 and the first pressure sensor 2 on the gas supply line 4, these different response values being adapted to different conditions of use of the insufflation device and being selected as required by means of the operating field 21 before the instrument is used. Examples of response values are 50 mm Hg for switch 26a (for use in laparoscopy), 90 mm Hg for switch 26b (for arthroscopy) and 210 mm Hg for switch 26c (for hysteroscopy). The response thresholds may, if desired, be varied by means of the operating field and the processing and control unit.

If the initial pressure in the gas supply line 4 exceeds the value selected by the user, the microcontroller 10.3 is activated by an output signal from the corresponding overpressure switch 26a, 26b or 26c, and the control stage 10.2 emits, at its command, control signals which close the pressure regulator (the proportional valve) 8 and the solenoid valve 13 (patient valve) at the exit from the gas supply line 4 and open up the outlet valve 14 to allow the excess pressure to escape. Once this has happened to overpressure switch "drops" back, the outlet valve 14 is closed again, the proportional valve 8 and the patient valve 13 are reopened and insufflation is continued. The response threshold of the exhaust valve can also be variable—in another embodiment—by means of software using the control unit.

In addition, the patient valve 13 and outlet valve 14 can be used to carry out a self test of the apparatus 1. With the patient valve 13 closed and the outlet valve 14 closed, a specific quantity of gas is able to flow, via the pressure regulating device 8, to the pressure sensors 2 and 3 and to the pressure switches 26 in order to monitor function. If the outlet valve 14 is opened while the patient valve 13 remains closed, the function of the gas flow measurement can be checked. The corresponding control calculations are made by the microcomputer 10.3 which opens up the apparatus 1 after a positive functional check by means of a suitable output signal and signals that it is ready on the operating field 21.

The processing and control unit 10 is subdivided in structure into the relatively independent blocks 10.1, 10.2, 10.3, and 10.4 (already mentioned hereinbefore to some extent) which carry out analogue signal processing (block 10.1—analogue processing stage), pressure control or safety switching (block 10.2—control stage), the running of the operating program and all necessary calculations (block 10.3—microcontroller) and the supply of current to the apparatus (block 10.4—current supply unit).

As already mentioned hereinbefore, the microcomputer 10.3 has an associated operating and display field 21 by means of which the user can choose the mode of operation or working range of the apparatus and which indicates all the measurements and operating parameters calculated which are relevant to the user.

Figure 2:
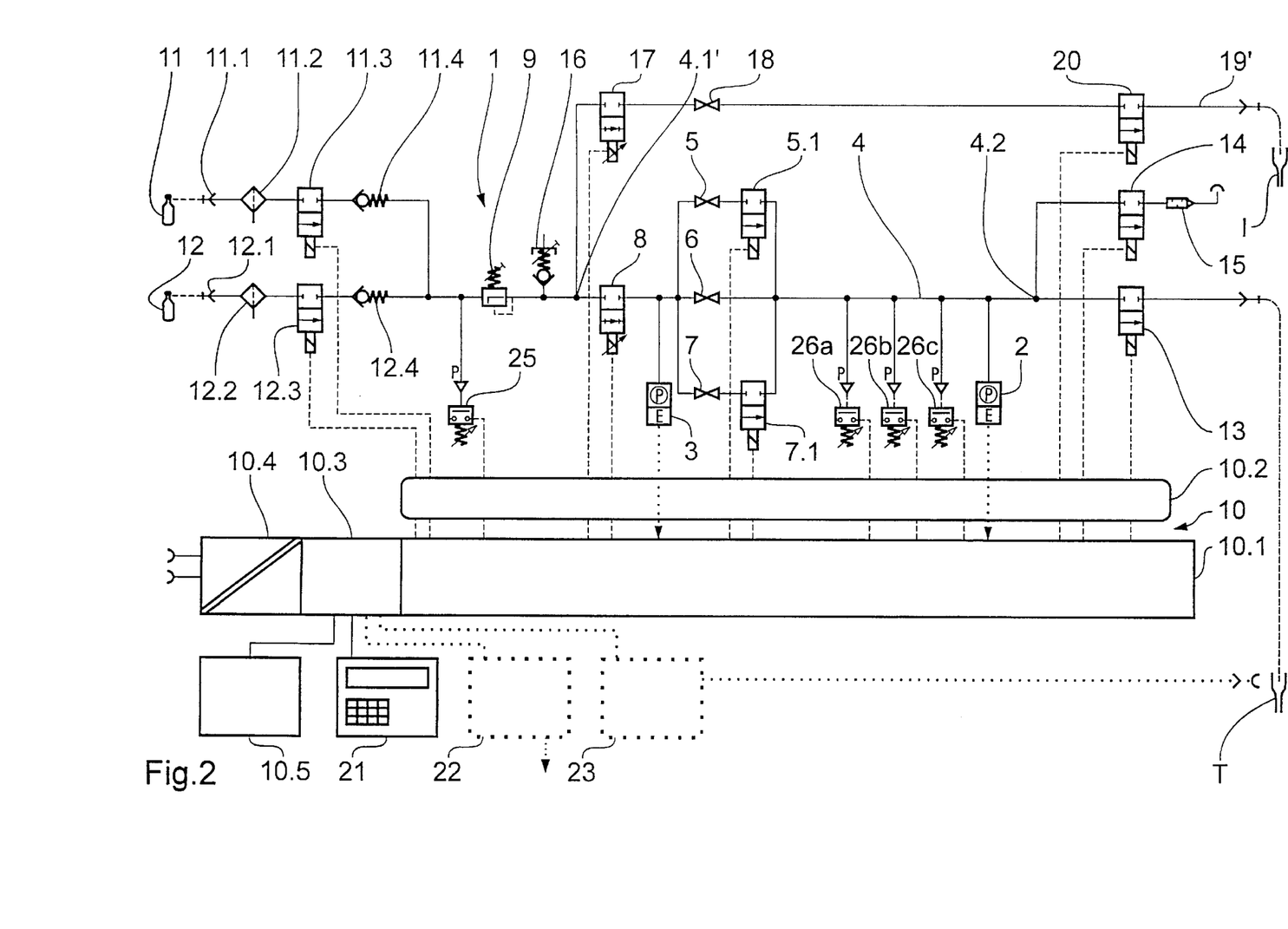
FIG. 2 is a favourable feature of the embodiment shown in FIG. 1.
Figure 3:
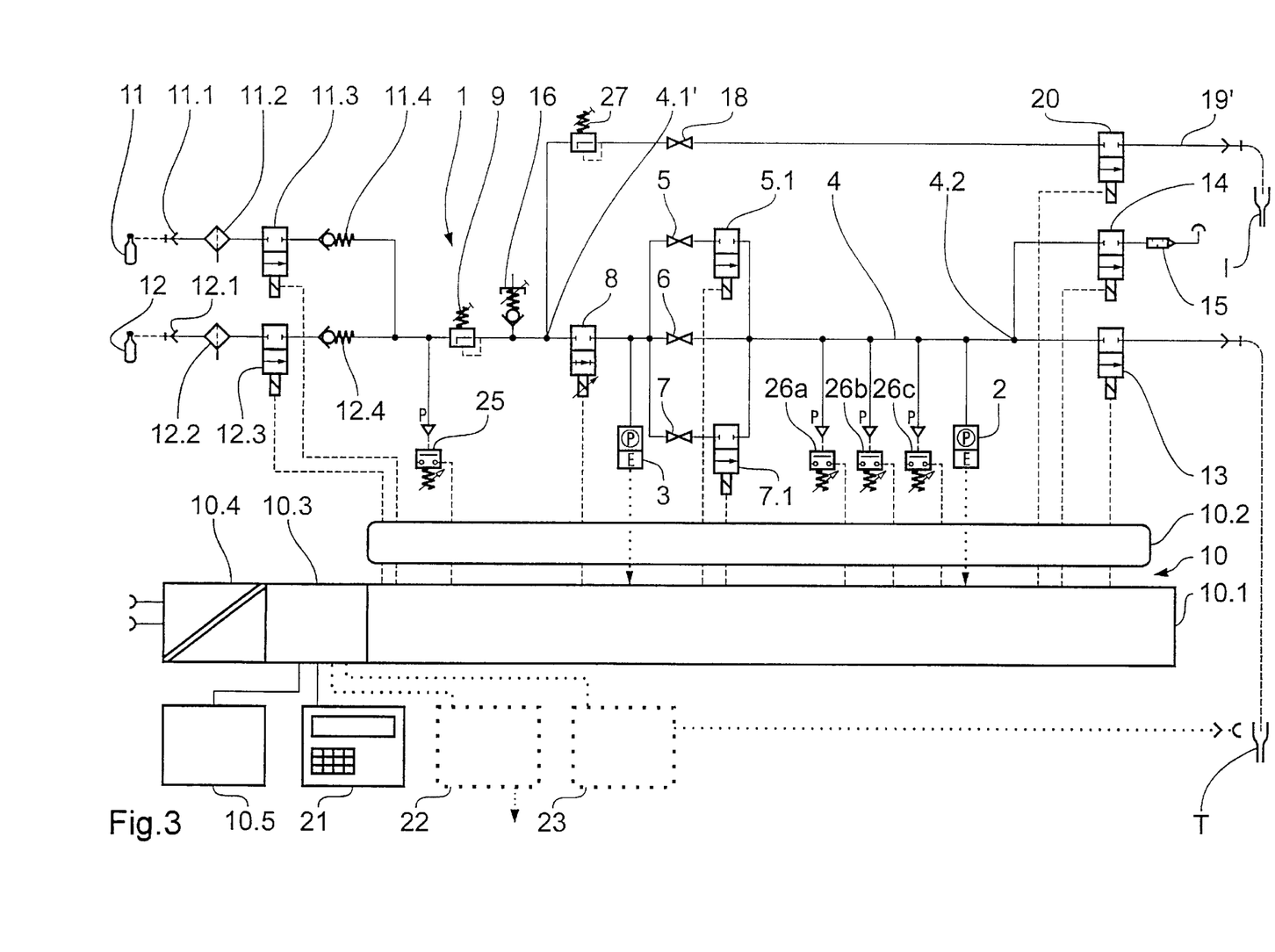
FIG. 3 is a further feature of the embodiment shown in FIG. 2.

In addition, the microcomputer 10.3 may also be associated with an interface 22 by means of which the operator can be given access to the measurements or operating parameters in the form of a video feedback into the image screen in order to observe the medical intervention, and a gas conditioning device 23 for heating, humidifying and/or filtering as necessary, which is indicated by dotted lines in the FIGS. 1–3. Any external gas conditioning provided may also be controlled by the processing unit 10 of the insufflation device 1.

Unlike the diagrammatic representation in FIG. 1, the gas conditioning may also be effective for the gas supplied to the medical instrument. This will be particularly useful when the quantity of gas introduced into the body has to be relatively great to ensure the necessary internal pressure of the instrument, because of the construction of the instrument.

FIGS. 2 and 3 show alternatives to the embodiment shown in FIG. 1 of an insufflation device in which the branch point 4.1' to the second tube branch 19' is located in the direction of flow between the overpressure safety device 16 of the high pressure reducer 9 and the proportional valve 8 provided in order to control the pressure or keep it constant, i.e. downstream thereof. In this case, a separate branch point 4.2 is provided for the outlet valve 14.

Thus, the proportional valve 8 and hence the pressure control or regulation for the actual insufflation is not effective for the tube branch 19'; the pressure separation from the main gas supply line 4 provides a simple and advantageous manner of separately setting or limiting the pressure for the instrument insufflation independently of the pressure levels selected for the expansion insufflation through the trocar T.

In the embodiment shown in FIG. 2, a separate proportional valve 17 is provided for this purpose, which is electrically operated by means of the processing and control unit 10 (and hence from the operating field 21), whereas in the embodiment shown in FIG. 3 there is only one simple pressure reducer 27.

The flow limiter 18 ensures that the gas throughput to the instrument I which is to be kept clean cannot become so great as to make the handling of the instrument difficult by an excessive escape of gas.

Figure 4:
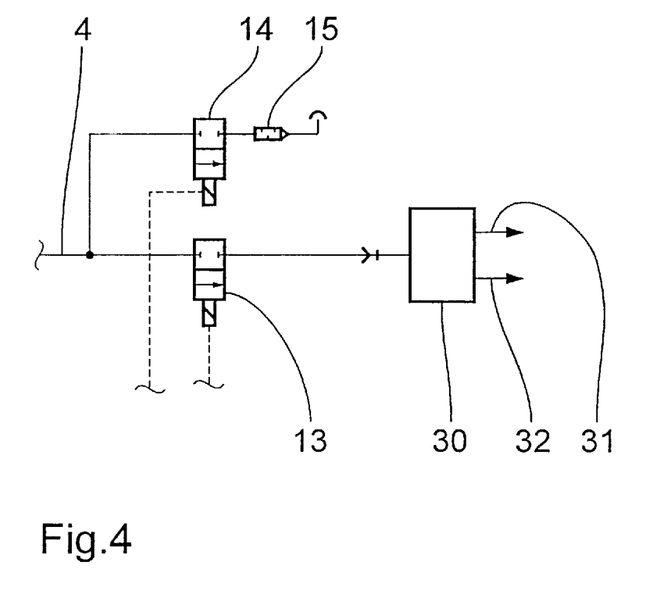
FIG. 4 is another advantageous embodiment of the invention.
Figure 5:
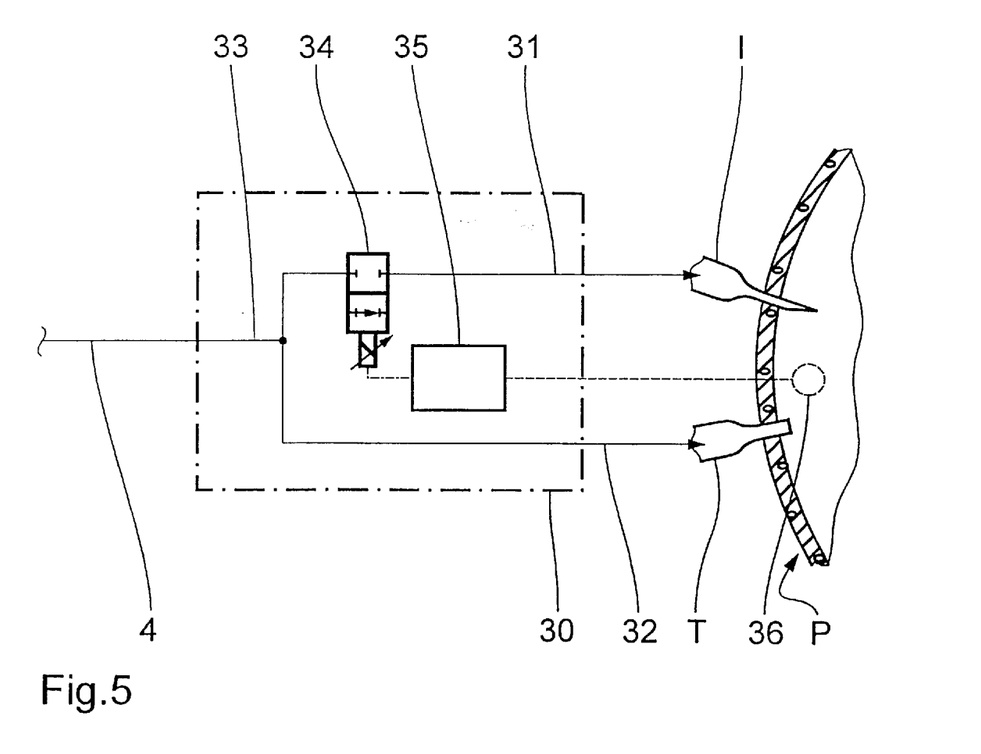
FIG. 5 is a further feature of the embodiment shown in FIG. 4.

The embodiment of the apparatus for performing the process according to the invention as illustrated diagrammatically in FIGS. 4 and 5 is an additional device 30 which is mounted in addition to the actual insufflation device, i.e. externally thereof, and is connected to the free end of the gas supply line 4 thereof.

It has an inflow channel 33 which is connectable to the tube connection and divides into two outflow channels 31, 32 for attachment to a first gas supply line for a surgical instrument I which is to be insufflated and a second gas supply line for an insufflation trocar T. Thus, a conventional insufflation arrangement can be used at the same time for instrument insufflation (with the same pressure level).

The embodiment sketched in FIG. 5 is suitable for those applications in which a separate pressure setting is desired for the instrument insufflation. Here, a proportional vale 34 is provided in the outflow channel 31 and this valve is connected via a control line to the output of a pressure control unit 35 which in turn is optionally connected at the input and to the output of a pressure sensor 36 (shown by doted lines) at the insufflated body cavity of a patient P in which the distal ends of the insufflation trocar T and of the instrument I are located.

Thus, for measuring the pressure in order to set the gas pressure of the instrument correctly, a separate pressure measuring channel is provided, since the pressure measurement in the "mother device" cannot readily be used to adjust the instrument pressure. In addition, this can also be used as an additional safety device to prevent an unintentional build up of excess pressure in the body of the patient.

However, with a combined apparatus as in the embodiments shown in FIGS. 1 to 3 and also with an add-on device as shown in FIGS. 4 or 5, it is also possible to provide a pressure sensor on the fluid (gas) line to the instrument by means of which the pressure can be at least approximately detected and monitored.

The process according to the invention may also be carried out as such using a conventional gas supply device with means for adjusting the gas pressure. In particular, an existing insufflation device may be used for this purpose, which may possibly be used exclusively for special applications in which there is no need for expansion insufflation, exclusively for the purpose of instrument insufflation.

Figure 6:
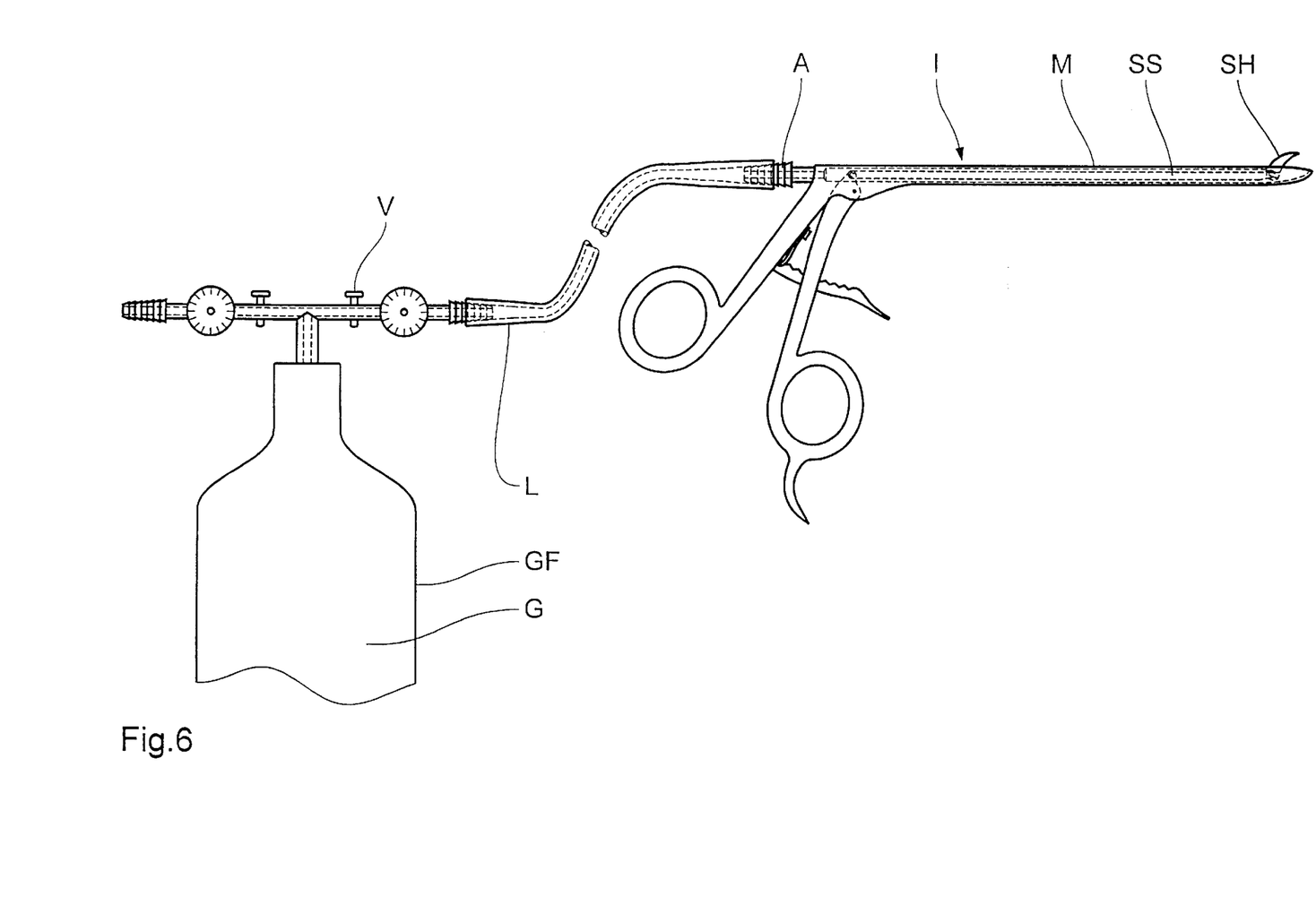
FIG. 6 is a diagrammatic view of a surgical instrument for the minimally invasive procedures which is connected to a fluid store.

A simple construction is shown in FIG. 6. A surgical cutting instrument I for minimally invasive surgery—e.g. in the joint region (for arthroscopy)—has a gas connection A which is formed as a continuation of the outer instrument sleeve or casing and allows gas to be introduced into all the crevices and cavities of the instrument. Attached to connection A is a gas hose L which is connected at the other end to a $CO_2$ gas bottle GF via a control valve V (which in this case is manually operated) and is fed with carbon dioxide gas G from the gas bottle when the arthroscopic cutting device I is used.

As is merely diagrammatically sketched in the FIG. 6, the carbon dioxide G introduced through the nozzle A under a preset pressure penetrates into the annular gap between the casing M of the instrument I and the bush rod SS sliding therein in order to actuate the cutting lever SH, fills the latter, whilst washing over the rotary bearings and other guides, etc.—and exits through the distal end of the instrument.

Instruments of different constructions, e.g. including electrically or optically operating instruments (especially electrical or laser ablation or coagulation instruments) are kept clean in a similar manner; in this case the gaps between individual current supplies and electrical connectors or between the light transmission elements and optical coupling members and between the casing or guides and these elements are flushed out. What is important in each case is that, by suitable construction of the instrument, a fluid connection is provided between all the gaps and cavities produced during manufacture, which may possibly come into contact with body fluid or gas from the patient's body, and the gas connection for the cleansing fluid.

The invention is not restricted to the preferred embodiments described above by way of example. Rather, a number of variants are conceivable which make use of the solution as described whilst employing fundamentally different embodiments.

We claim:

1. Process for maintaining the sterility of the inner cavity of a medical operating instrument (I) having an outer casing (M) and operating or actuating elements (SS, SH) arranged therein, said instrument being used to enter the body of a living person or animal, comprising the step of cleaning said instrument during use of the instrument, wherein said cleaning step further comprises the substeps of introducing a medically clean fluid (G) during use of the instrument substantially to a proximal end of the instrument through a fluid connection (A) in such a way that essentially all crevices and cavities in an inner space of the instrument, in fluid contact with the inside of the body, between the operating or actuating elements (SS, SH) and the casing (M) are filled with the fluid, and maintaining a flow of said medically clean fluid substantially to a proximal end of the instrument through a fluid connection (A) in such a way that essentially all crevices and cavities in an inner space of the instrument, in fluid contact with the inside of the body, between the operating or actuating elements (SS, SH) and the casing (M) remain filled with the fluid during substantially the entire period of use of said instrument.

2. Process according to claim 1, wherein the fluid (G) is a gas at a pressure above atmospheric pressure.

3. Process according to claim 2, wherein the the substep of introducing the gas takes place parallel to an expanding insufflation with gas using the same gas or the expansion insufflation is carried out simultaneously through the medical instrument (I).

4. Process according to claim 3, wherein the pressure of the gas used during the introducing substep is controlled as a function of an internal pressure set in the body of a living person or animal during insufflation or insufflation pressure measured at an apparatus used for expanding a body part of the living person or animal.

5. Process according to claim 2, wherein the gas is carbon dioxide.

* * * * *